United States Patent
Moore et al.

(10) Patent No.: US 11,067,550 B2
(45) Date of Patent: Jul. 20, 2021

(54) HEAVIER ISOTOPE GAS VARIANTS AS CALIBRATION GAS MINOR COMPONENTS

(71) Applicants: Ferrel D. Moore, Lincoln Park, MI (US); James Robert Moore, Lincoln Park, MI (US)

(72) Inventors: Ferrel D. Moore, Lincoln Park, MI (US); James Robert Moore, Lincoln Park, MI (US)

(73) Assignee: Ferrel D. Moore, Lincoln Park, MI (US)

( * ) Notice: Subject to any disclaimer, the term of this patent is extended or adjusted under 35 U.S.C. 154(b) by 515 days.

(21) Appl. No.: 15/946,200

(22) Filed: Apr. 5, 2018

(65) Prior Publication Data

US 2018/0292372 A1 Oct. 11, 2018

Related U.S. Application Data

(60) Provisional application No. 62/481,921, filed on Apr. 5, 2017.

(51) Int. Cl.
*G01N 33/00* (2006.01)
*G01N 27/416* (2006.01)

(52) U.S. Cl.
CPC ..... *G01N 33/0006* (2013.01); *G01N 27/4163* (2013.01); *Y10T 436/100833* (2015.01)

(58) Field of Classification Search
CPC .... F17C 1/10; F17C 1/005; F17C 1/02; F17C 1/04; F17C 1/14; Y10T 436/100833; G01N 33/0006; G01N 27/4163; G01N 33/0008

See application file for complete search history.

(56) References Cited

U.S. PATENT DOCUMENTS

2008/0011952 A1* 1/2008 Fabinski ............ G01N 21/3504
250/344

FOREIGN PATENT DOCUMENTS

DE 222 353 A1 * 5/1985

OTHER PUBLICATIONS

Moore, J. "Calibration: Who Needs It?" Occupational Health and Safety Magazine. Oct. 14, 2010. Downloaded from <https://www.idealcalibrations.com/gas-detector-blog/2010/10/14/article-calibration-who-needs-it-by-james-moore-occupational.html> on Aug. 31, 2020 (Year: 2010).*

"Ionic bond," IUPAC. Compendium of Chemical Terminology, 2nd ed. (the "Gold Book"). Compiled by A. D. McNaught and A. Wilkinson. Blackwell Scientific Publications, Oxford (1997). (Year: 1997).*

Socki, R. et al. "Enhanced Stability of Stable Isotopic Gases," ACS Omega 2020, 5, 29, 17926-17930 (Year: 2020).*

(Continued)

*Primary Examiner* — Christopher Adam Hixson
*Assistant Examiner* — Michelle Adams
(74) *Attorney, Agent, or Firm* — Quinn IP Law

(57) ABSTRACT

A method for providing a calibration test gas sample includes identifying a first test canister containing a standard test gas including an ionic gas. A chemical formulation of the standard test gas includes a cation and an anion. The method further includes replacing the first test canister with a second test canister containing an improved test gas. A chemical formulation of the improved test gas includes a replacement atom comprising one of a heavier isotope of one of the cation and the anion.

5 Claims, 2 Drawing Sheets

(56) References Cited

OTHER PUBLICATIONS

Jacksier, T. et al. "Gaseous Calibration Standards: Manufacturing, Stability, Traceability and Uncertainty," Offshore Technology Conference, Houston, Texas, USA, May 1-4, 2017; uploaded to ResearchGate on Apr. 22, 2017. (Year: 2017).*
Benesch, R. et al. "The Stability of 100 ppb Hydrogen Sulfide Standards," Anal. Chem. 2004, 76, 7396-7399 (Year: 2004).*
GasAlertMicro 5/PID/IR User Manual. BW Technologies by Honeywell. (2009) (Year: 2009).*

* cited by examiner

HEAVIER ISOTOPE GAS VARIANTS AS CALIBRATION GAS MINOR COMPONENTS

CROSS-REFERENCE TO RELATED APPLICATIONS

This disclosure claims priority to U.S. Provisional Patent Application 62/481,921 filed on Apr. 5, 2017, which is hereby incorporated by reference.

TECHNICAL FIELD

This disclosure is related to creating a stable calibration gas mixture for calibration of gas testing equipment.

BACKGROUND

The statements in this section merely provide background information related to the present disclosure. Accordingly, such statements are not intended to constitute an admission of prior art.

Gas test machines or monitors are used to test for presence of a particular gas in an area. For example, in factories or refineries, it can be important to test whether any of the chemicals being manufactured are leaking from the production equipment. These monitors must be calibrated frequently to ensure that the tests run by the monitors are accurate.

There are a variety of gases used to calibrate gas test machines or monitors. Some of these have the tendency to react with the interior wall of the cylinder in which they are contained. Some of these gases, such as hydrogen sulfide, also have a tendency to oxidize in gas mixtures with sufficient oxygen present, sufficient temperature and perhaps the presence of a metallic catalyst. From the standpoint of both manufacturer and user, this is in general called "fade."

For example, if a gas blender prepares a gaseous standard of 10 ppm $H_2S$ balance air, even though the mixture is accurately made, it is easy to see that even a small amount of oxidation or catalyzed reaction which causes even 2 ppm of the $H_2S$ mix to fade, mathematically that represents a 20% drop in concentration, which is unacceptable. Even though the product was made, analyzed and shipped, by the time it gets to the customer it could drop that much and more. Hydrogen sulfide is not the only compound which does this, there are others as well, such as $NH_3$ (ammonia) and $Cl_2$ (chlorine) et al.

SUMMARY

A method for providing a calibration test gas sample includes identifying a first test canister containing a standard test gas including an ionic gas. A chemical formulation of the standard test gas includes a cation and an anion. The method further includes replacing the first test canister with a second test canister containing an improved test gas. A chemical formulation of the improved test gas includes a replacement atom comprising one of a heavier isotope of one of the cation and the anion.

BRIEF DESCRIPTION OF THE DRAWINGS

One or more embodiments will now be described, by way of example, with reference to the accompanying drawings, in which.

DETAILED DESCRIPTION

Figure 1:
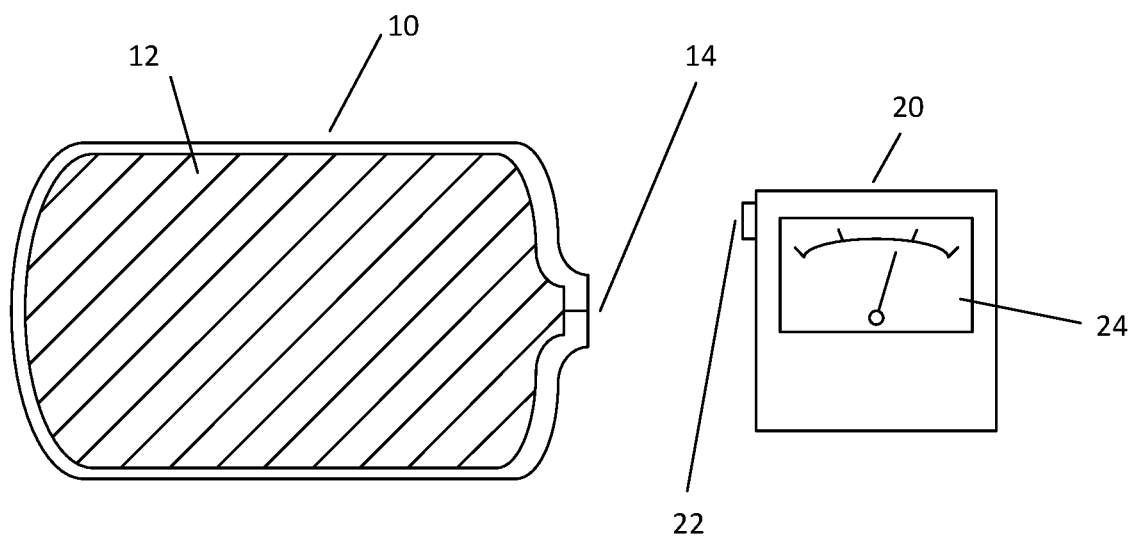
FIG. 1 illustrates exemplary testing of a monitor with a known hydrogen sulfide cylinder, in accordance with the present disclosure.

Ionic gas molecules include reactive atoms that are joined together with an ionic bond. At least one cation with a positive charge joins with at least one anion with a negative charge. While the ionic molecules exist as a neutral molecule, with the positive and negative charges, it is known in the art that some small fraction of ionic molecules in a sample break apart over time, leaving the separated cations and anions to react with nearby materials. If a container holding a sample including ionic gas molecules is constructed with materials that can react with the cations or anions in the sample or if oxygen is present in the test gas mixture, the concentration of the ionic gas molecules can degrade over time.

Testing has shown that heavier atom isotopes tend to be less reactive in an ionic gas molecule sample.

Further, some covalently bonded molecules can be identified as strong oxidizing agents. Such strong oxidizing agents can similarly be made less reactive by utilizing heavier isotopes of the atoms in the oxidizing agent. Replacing standard chlorine gas, $^{35}Cl_2$, with $^{37}Cl_2$ can in this way create an improved test gas sample, slowing the fade process in the gas sample. Other strong oxidizing agents that can be made less reactive by utilizing heavier isotopes include NO, nitric oxide, and $NO_2$, nitrogen dioxide.

A method is disclosed to replace unstable test gases with stable test gases that can be used to accurately simulate test results in a corresponding monitor calibrated to look for the presence of the test gases. The disclosed method includes exemplary replacement of a standard cation or anion in a test gas with a heavier isotope of the cation or anion. In a specific example, the disclosed method includes exemplary replacement of standard ammonia and hydrogen sulfide gas mixtures (and other relevant gas mixtures with hydrogen as part of the molecular make up) with a deuterated variant to improve mixture stability. To say it another way, the general principal is that in reactive compounds such as $NH_3$, $H_2S$, $PH_3$, (known as phosphine), HCN (known as hydrogen cyanide), et al., we replace hydrogen with deuterium. Electrochemical detectors cannot differentiate between the two when integrated into a compound. For example, such is the case when 25 ppm $D_2S$/balance air is compared to 25 ppm $H_2S$/balance air using an electrochemical detector. The extra neutron in the deuterium over that of hydrogen, however, slows down the reaction with the cylinder wall and valve interface. This contributes to gas mixture stability for those mixtures in question.

In another example, in ionic test gases including chlorine-35, a substitute test gas including the heavier isotope chlorine-37 can be used. The heavier chlorine isotope is more stable and maintains the desired concentration in a test canister longer than the lighter isotope.

A method for reducing this "fade" for those compounds containing hydrogen (such as $H_2S$ and ammonia), would be to substitute an isotopically enriched variant that is heavier than the main isotopic component. For example, the substitution of deuterium for hydrogen. Deuterium contains an extra neutron that hydrogen does not, thereby making it heavier. The molecular weight of deuterium sulfide is heavier than hydrogen sulfide. The molecular weight of deuterated ammonia is heavier than ammonia. This is advantageous when preparing calibration gases of both hydrogen sulfide and ammonia because the extra weight of the additional neutrons means a higher activation energy has to be achieved for either oxidation or catalysis to occur. This reduces the potential for reaction in the cylinder and thus reducing the potential for fade, improving the stability of the reactive gas mixture in question. Therefore, gaseous standards would be more likely to retain their integrity for a longer period of time, increasing their shelf life.

Yet because these isotopically enriched gas substitutions are isotopes, they retain the chemical identity and properties. Deuterium sulfide is still hydrogen sulfide, just a little heavier. The same can be said for deuterated ammonia—it is still ammonia. There are certain chemical analyzers that can detect the difference (mass spectrometer for example), but the electrochemical cells used in the main in the personal safety market (portable gas detectors) which use electrochemical cells cannot differentiate between one and the other. This is to say that a mixture of 10 ppm $H_2S$/balance air reads the same as a mixture of 10 ppm $D_2S$ in air. The same is true for deuterated ammonia versus ammonia.

In simple terms, the idea of substituting heavier isotopic variants (which generally represent a smaller portion of the total isotope composition of an element or compound), is to improve the gas mixtures stability by retarding its reaction threshold.

This principle also holds true for aqueous and material standards subject to reactivity issues as well. The limitation is that the instruments using them as standards must not be able to detect the difference.

Referring now to the drawings, wherein the showings are for the purpose of illustrating certain exemplary embodiments only and not for the purpose of limiting the same, FIG. 1 illustrates exemplary testing of a monitor with a known hydrogen sulfide cylinder. Cylinder 10 illustrated including a known concentration 12 of $H_2S$ and output valve 14 calibrated to provide a particular test result upon monitor 20. Monitor 20 includes test port 22 and meter output 24.

Figure 2:
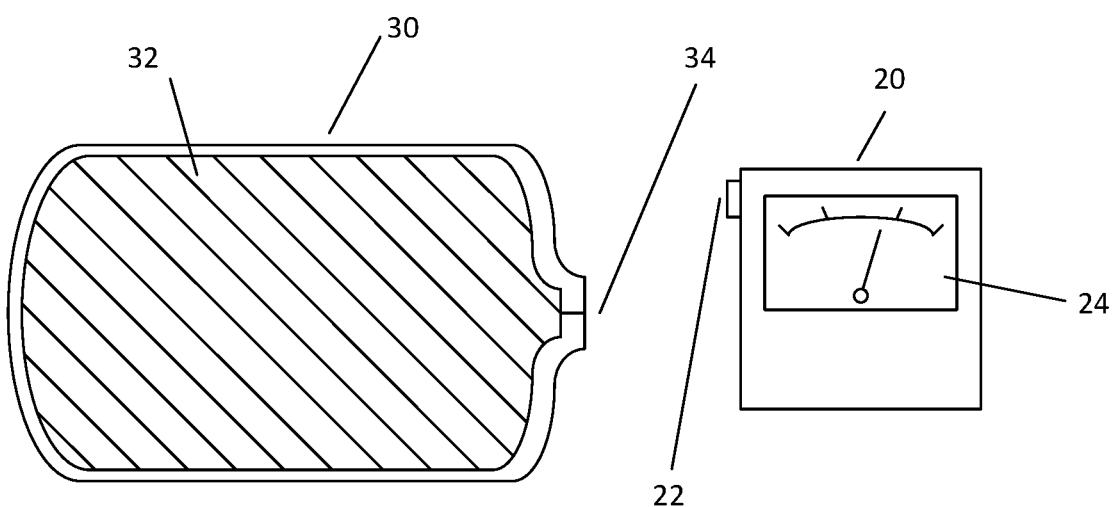
FIG. 2 illustrates exemplary testing of the monitor of FIG. 1, with a substitute test cylinder substituting deuterium sulfide for hydrogen sulfide, in accordance with the present disclosure.

FIG. 2 illustrates exemplary testing of the monitor of FIG. 1, with a substitute test cylinder substituting deuterium sulfide for hydrogen sulfide. Cylinder 30 illustrated including a known concentration 32 of $D_2S$ and output valve 34 calibrated to provide a particular test result upon monitor 20. Monitor 20 includes test port 22 and meter output 24. By replacing $H_2S$ with an equivalent concentration of $D_2S$, a same or substantially equivalent meter result upon monitor 20 can be achieved.

Figure 3:
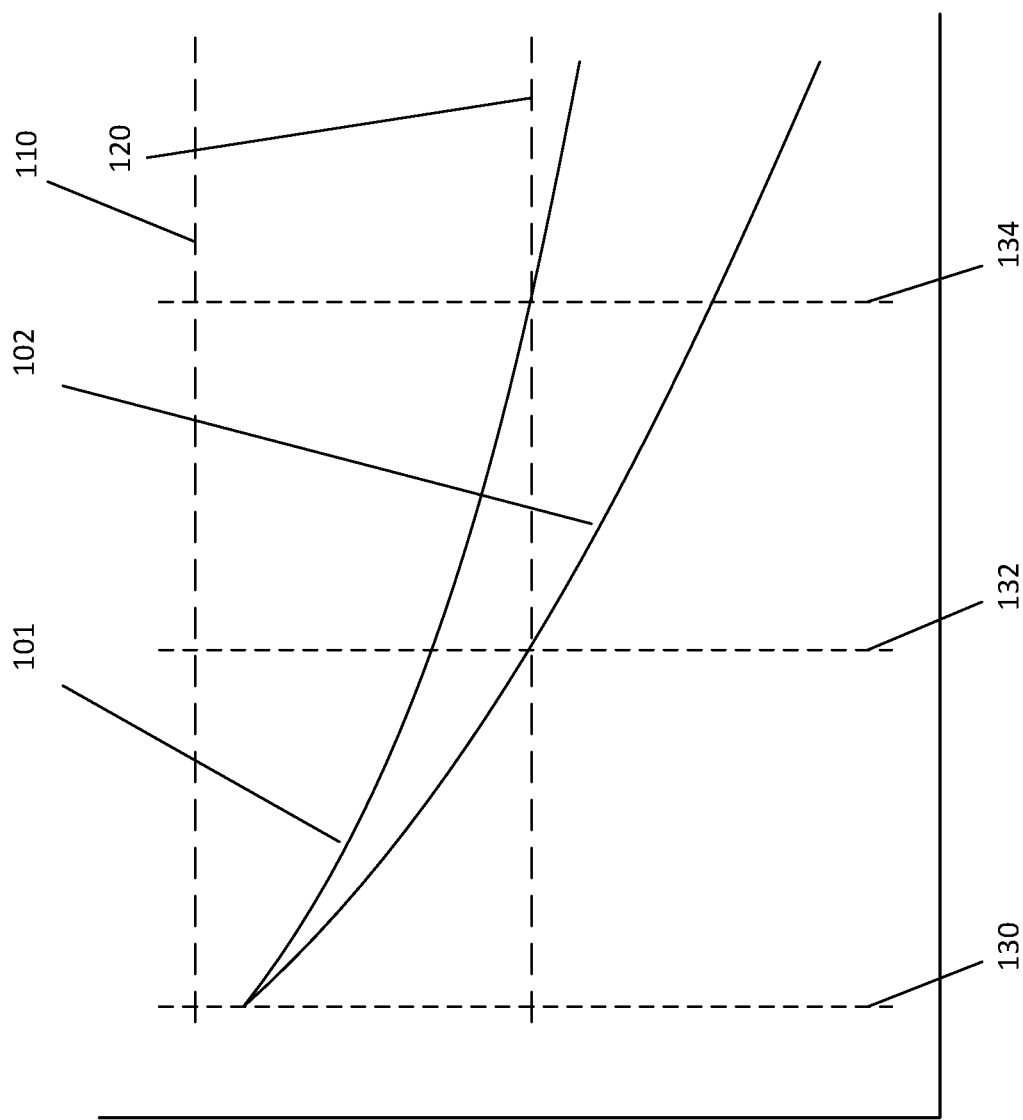
FIG. 3 illustrates in a graphical data plot exemplary test readings illustrating fade in a standard test gas canister and fade in a test gas canister improved with a heavy isotope, in accordance with the present disclosure.

FIG. 3 illustrates in a graphical data plot exemplary test readings illustrating fade in a standard test gas canister and fade in a test gas canister improved with a heavy isotope. A vertical axis is defined illustrating test gas concentration values. A horizontal axis is defined illustrating changing time values. Plot 102 is illustrated showing a concentration reading over time of a standard sample including ionic gas molecules in a standard test gas. Plot 101 is illustrated showing a concentration reading over time of an improved sample including ionic gas molecules in an improved test gas. The test gas in plot 101 is identical to the test gas in plot 102, except that the test gas in plot 101 substitutes a standard cation or anion in the test gas in plot 102 with a heavier isotope of the cation or anion. Both plots illustrate a typical exponential decay typical to fade in a test gas. Both test gases are contained within a substantially identical test canister. Horizontal line 110 illustrates a maximum concentration acceptable for the test canisters. Horizontal line 120 illustrates a minimum concentration acceptable for the test canisters. When either plot 101 or plot 102 fall below horizontal line 120, the test canister is said to be exhausted or at the end of its useful test life. Vertical line 130 illustrates a test start time, where both test canisters start with a same concentration of the test gases. Vertical line 132 illustrates a time at which plot 102 falls below line 120. Vertical line 134 illustrates a time at which plot 101 falls below line 120. Fade illustrated in plot 102 causes the standard test gas to relatively rapidly fall below line 120, indicating that the standard test gas is at the end of its useful test life. As described herein, the heavier isotope in the improved test gas illustrated in plot 101 causes the fade illustrated in plot 101 to relatively slowly fall below line 120, indicating that the improved test gas has a longer useful test life than the standard gas sample.

The disclosure has described certain preferred embodiments and modifications of those embodiments. Further modifications and alterations may occur to others upon reading and understanding the specification. Therefore, it is intended that the disclosure not be limited to the particular embodiment(s) disclosed as the best mode contemplated for carrying out this disclosure, but that the disclosure will include all embodiments falling within the scope of the appended claims.

The invention claimed is:

1. A method for providing a calibration test gas sample, comprising:
   identifying a first test canister containing a standard test gas, wherein the standard test gas comprises standard hydrogen sulfide; and
   replacing the first test canister with a second test canister containing an improved test gas, wherein the improved test gas comprises a deuterated variant of hydrogen sulfide,
   wherein hydrogen sulfide in the improved test gas is isotopically enriched in deuterium compared to hydrogen sulfide in the standard test gas, and
   wherein the second test canister has a concentration of the deuterated variant of hydrogen sulfide that is equivalent to a concentration of the standard hydrogen sulfide in the first test canister.

2. A method for providing a calibration test gas sample, comprising:
   identifying a first test canister containing a standard test gas, wherein the standard test gas comprises standard ammonia; and
   replacing the first test canister with a second test canister containing an improved test gas, wherein the improved test gas comprises a deuterated variant of ammonia,
   wherein ammonia in the improved test gas is isotopically enriched in deuterium compared to ammonia in the standard test gas, and
   wherein the second test canister has a concentration of the deuterated variant of ammonia that is equivalent to a concentration of the standard ammonia in the first test canister.

3. A method for providing a calibration test gas sample, comprising:
   identifying a first test canister containing a standard test gas, wherein the standard test gas comprises an oxidizing agent; and replacing the first test canister with a second test canister containing an improved test gas, wherein the improved test gas comprises an isotopically enriched variant of the oxidizing agent that is enriched in a heavier isotope of an atom in the oxidizing agent as compared to the oxidizing agent in the standard test gas, and wherein the second test canister has a concentration of the isotopically enriched variant of the oxidizing agent that is equivalent to a concentration of the oxidizing agent in the first test canister.

4. The method of claim 3, wherein the oxidizing agent comprises chlorine gas.

5. The method of claim 3, wherein the oxidizing agent comprises nitrogen dioxide.

* * * * *